US012141994B2

(12) United States Patent
Fialkov et al.

(10) Patent No.: US 12,141,994 B2
(45) Date of Patent: Nov. 12, 2024

(54) SYSTEMS AND METHODS FOR ASSESSMENT OF NASAL DEVIATION AND ASYMMETRY

(71) Applicant: SUNNYBROOK RESEARCH INSTITUTE, Toronto (CA)

(72) Inventors: Jeffrey Allan Fialkov, Toronto (CA); Cari Marisa Whyne, Toronto (CA); Jacob Zachary Fishman, North York (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 524 days.

(21) Appl. No.: 17/400,807

(22) Filed: Aug. 12, 2021

(65) Prior Publication Data
US 2022/0051428 A1 Feb. 17, 2022

Related U.S. Application Data

(60) Provisional application No. 63/065,425, filed on Aug. 13, 2020.

(51) Int. Cl.
*G06T 7/68* (2017.01)
*A61B 5/00* (2006.01)
(Continued)

(52) U.S. Cl.
CPC .............. *G06T 7/68* (2017.01); *A61B 5/0064* (2013.01); *A61B 5/0077* (2013.01); *A61B 5/103* (2013.01);
(Continued)

(58) Field of Classification Search
CPC . G06T 7/68; G06T 7/337; G06T 2207/30004; G06T 2207/30201;
(Continued)

(56) References Cited

U.S. PATENT DOCUMENTS

| 11,589,949 | B1 * | 2/2023 | Mills | A61B 5/0037 |
| 2014/0152956 | A1 * | 6/2014 | Silva | G02C 13/003 |
| | | | | 351/204 |

(Continued)

OTHER PUBLICATIONS

Al-Rudainy, D. et al., "Assessment of regional asymmetry of the face before and after surgical correction of unilateral cleft lip", J. Cranio-Maxillo-Facial Surg. 46, 974-978, 2018.
(Continued)

*Primary Examiner* — Dhaval V Patel
(74) *Attorney, Agent, or Firm* — HILL & SCHUMACHER

(57) ABSTRACT

Systems and methods are provided for assessing nasal deviation and symmetry via the processing of facial surface data. Facial surface data may be processed to determine a nasal deviation measure indicative of a lateral deviation between a nasal midline and a facial midplane. The facial surface data may also be processed to determine a measure of nasal symmetry associated with a selected nasal surface region, such as an aesthetic subunit. Nasal deviation and symmetry information based on both measures may then be presented. In some example implementations, a single nasal symmetry measure is generated and present for a given nasal surface region. Reference surface data characterizing a reference symmetrical facial shape and having a defined facial direction relative to a coordinate system may be employed to align the facial surface data prior to the determination of the nasal deviation and nasal symmetry measures.

20 Claims, 16 Drawing Sheets

(51) Int. Cl.
 *A61B 5/103* (2006.01)
 *A61B 90/00* (2016.01)
 *G06T 7/33* (2017.01)

(52) U.S. Cl.
 CPC .............. *A61B 5/742* (2013.01); *A61B 90/36* (2016.02); *G06T 7/337* (2017.01); *A61B 2090/365* (2016.02); *G06T 2207/30004* (2013.01); *G06T 2207/30201* (2013.01)

(58) Field of Classification Search
 CPC ........ G06T 2207/10028; A61B 5/0064; A61B 5/0077; A61B 5/103; A61B 5/742; A61B 90/36; A61B 2090/365; A61B 2034/105; A61B 5/1072; A61B 5/1075; A61B 5/1079
 See application file for complete search history.

(56) References Cited

U.S. PATENT DOCUMENTS

| | | | | |
|---|---|---|---|---|
| 2017/0316582 | A1* | 11/2017 | Chen | H04N 23/66 |
| 2020/0197137 | A1* | 6/2020 | Xia | A61B 34/20 |
| 2023/0200908 | A1* | 6/2023 | Sweis | G16H 50/20 |
| | | | | 705/2 |

OTHER PUBLICATIONS

Amornvit, P. et al., "The Accuracy of Digital Face Scans Obtained from 3D Scanners: An In Vitro Study", Int. J. Environ. Res. Public Health 16, 1-13, 2019.

Coghlan, B. A. et al., "A computer-aided method of measuring nasal symmetry in the cleft lip nose", Brit. J. Plas. Surg. 46, 13-17, 1993.

Desmedt, D. et al., "Nasolabial symmetry and esthetics in cleft lip and palate; analysis of 3D facial images", Clin Oral Invest 19, 1833-1842, 2015.

Kimura, N. et al., J., "Three-dimensional analyses of nasolabial forms and upper lip surface symmetry after primary lip repair in patients with complete unilateral cleft lip and palate", Cranio-Maxillo-Facial Surg. 47, 245-254, 2019.

Koban, K. et al., "Validation of two handheld devices against a non-portable three-dimensional surface scanner and assessment of potential use for intraoperative facial imaging", J. Plas. Reconst. Aesth. Surg. 73, 141-148, 2019.

Linden, O. et al., "Three-Dimensional Analysis of Nasal Symmetry Following Primary Correction of Unilateral Cleft Lip Nasal Deformity", Cleft Plate-Crain. J. 54, 715-719, 2017.

Taylor, H. et al., "Quantitative Facial Asymmetry: Using Three-Dimensional Photogrammetry to Measure Baseline Facial Surface Symmetry", J. Crain. Surg. 25, 124-128, 2014.

Zhao, Y. et al., "Three-Dimensional Accuracy of Facial Scan for Facial Deformities in Clinics: A New Evaluation Method for Facial Scanner Accuracy", PLOS One 12, 1-13, 2017.

"The application of Augmented Reality in esthetic medicine and plastic surgery", Transition Technologies PSC Website, Wayback Machine, 2019.

Fishman, Z. et al., "Assessing nasal symmetry with 3D scanning for reconstructive & cosmetic plastic surgery", 16th International Symposium on Computer Methods in Biomechanics & Biomedical Engineering (CMBBE), 2019.

* cited by examiner

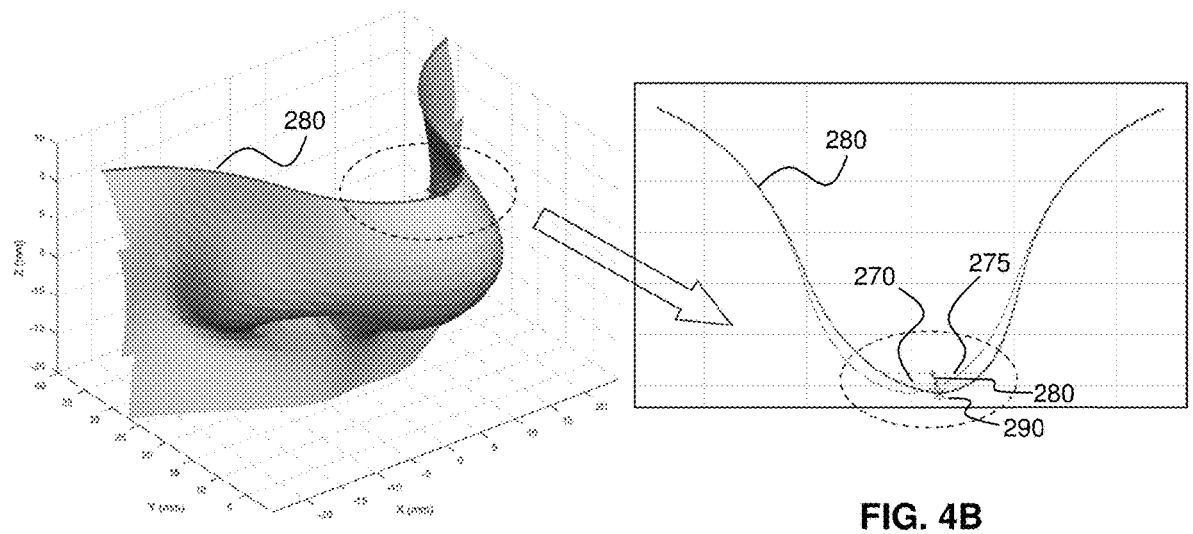
FIG. 4A
FIG. 4B
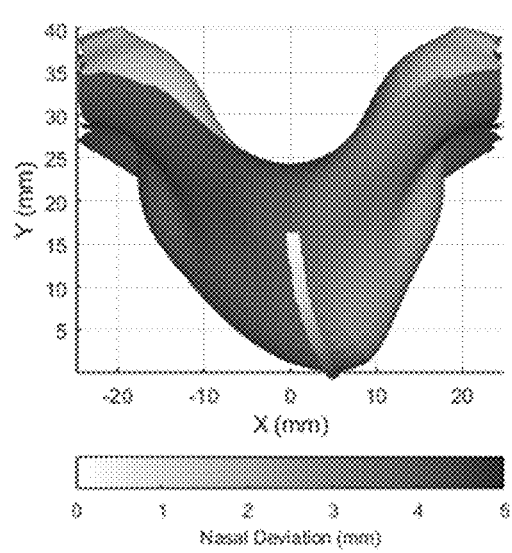
FIG. 5A
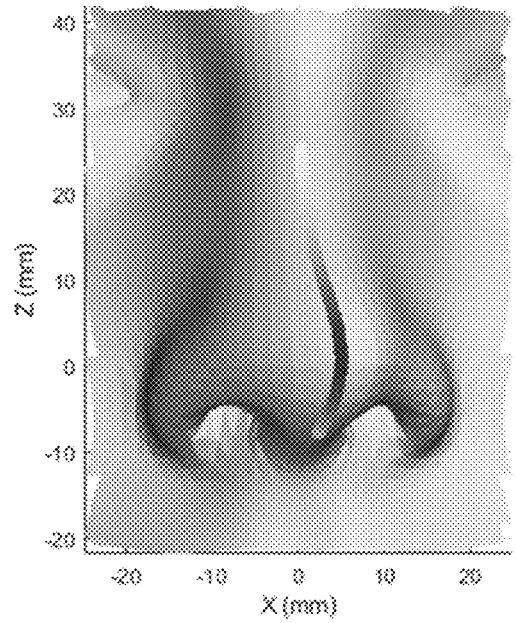
FIG. 5B

Measured along nose midline vs. just to nose-tip

SYSTEMS AND METHODS FOR ASSESSMENT OF NASAL DEVIATION AND ASYMMETRY

CROSS-REFERENCE TO RELATED APPLICATION

This application claims priority to U.S. Provisional Patent Application No. 63/065,425, titled "SYSTEMS AND METHODS FOR ASSESSMENT OF NASAL DEVIATION AND ASYMMETRY" and filed on Aug. 13, 2020, the entire contents of which is incorporated herein by reference.

BACKGROUND

The present disclosure relates to the facial detection and the determination of nasal deviation and asymmetry.

Nasal reconstruction exemplifies the challenges encountered in craniofacial reconstruction and highlights the opportunities for developing new technology. The nose is a facial feature in which millimeters of soft tissue changes can significantly affect the morphology. As such, accurate reconstruction of the outer soft tissue is critical following nasal trauma or pathology. In nasal reconstruction, vascularized 2D skin is grafted from the forehead to enable formation of the nose according to the 3D defect shape. A critical step in this procedure is templating the forehead flap shape corresponding to the specific defect. Accurate forehead flap shaping is necessary to obtain adequate cosmesis, symmetry and optimal function.

Nasal asymmetry beyond 2-3 mm is visually perceived, yet making adjustments to achieve optimal symmetry in the operative environment is challenging. Evaluating nasal symmetry is typically performed intra-operatively using a fully manual approach based only on a surgeons' visual perception for assessment. Such 'eyeballing' assessment must also be combined with the surgeons' ability to make small 3D adjustments to achieve nasal and facial symmetry. Together, current assessment and manipulation approaches are time-consuming and can result in inaccurate sub-optimal outcomes.

SUMMARY

Systems and methods are provided for assessing nasal deviation and symmetry via the processing of facial surface data. Facial surface data may be processed to determine a nasal deviation measure indicative of a lateral deviation between a nasal midline and a facial midplane. The facial surface data may also be processed to determine a measure of nasal symmetry associated with a selected nasal surface region, such as an aesthetic subunit. Nasal deviation and symmetry information based on both measures may then be presented. In some example implementations, a single nasal symmetry measure is generated and present for a given nasal surface region. Reference surface data characterizing a reference symmetrical facial shape and having a defined facial direction relative to a coordinate system may be employed to align the facial surface data prior to the determination of the nasal deviation and nasal symmetry measures.

Accordingly, in a first aspect, there is provided a method of assessing nasal symmetry, the method comprising:
employing a surface scanning device to acquire facial surface data of a facial region of a subject, the facial region including a nose of the subject;
processing the facial surface data to determine a nasal deviation measure indicative of a lateral deviation between a nasal midline of the subject and a facial midplane of the subject;
processing the facial surface data to determine a nasal symmetry measure indicative of a degree of symmetry associated with a nasal surface region relative to the facial midplane; and generating a display comprising nasal deviation and symmetry information, the nasal deviation and symmetry information being generated based on both the nasal deviation measure and the nasal symmetry measure.

In some example implementations, the method further comprises, prior to determining the nasal deviation measure and the nasal symmetry measure, performing surface registration of the facial surface data with reference surface data, the reference surface data characterizing a reference symmetrical facial shape and having a facial direction, in a direction perpendicular to a coronal plane, aligned with a selected coordinate system, thereby generating transformed facial surface data aligned with the selected coordinate system, wherein the facial midplane is associated with the reference surface data.

The facial surface data may further characterize the maxilla-mandibular region.

The method may further comprise, prior to performing surface registration, removing nasal surface data from the facial surface data.

In some example implementations, the nasal deviation measure may be determined according to a lateral difference, within a transverse plane, perpendicular to the facial direction, between an estimated maximal dorsal projection of the transformed facial surface data within the transverse plane and the facial midplane.

In some example implementations, the estimated maximal dorsal projection may be determined by:
generating a first segment extending laterally, within the transverse plane, perpendicular to the facial direction, and intersecting a nasal curve associated with the portion of the transformed facial surface data residing within the transverse plane at first intersection points, and obtaining a first midpoint location along the first segment between the first intersection points, the first segment being offset, in a posterior direction, by a first offset relative to a maximum anterior location of the nasal curve;
generating a second segment extending laterally, within the transverse plane, perpendicular to the facial direction, and intersecting the nasal curve at second intersection points, and obtaining a second midpoint location along the second segment between the second intersection points, the second segment being offset, in the posterior direction, by a second offset relative to the maximum anterior location of the nasal curve; and
determining the estimated maximal dorsal projection as the location of intersection between a third segment with the nasal curve, the first midpoint location and the second midpoint location residing on the third segment.

In some example implementations, the nasal deviation measure may comprise a plurality of lateral differences, each lateral difference being determined within a separate transverse plane. The nasal deviation and symmetry information may comprise a nasal midline curve generated based on the plurality of lateral differences.

In some example implementations, the nasal symmetry measure is determined by:
processing the nasal surface region to generate a mirrored nasal surface region, the mirrored nasal surface region residing on a contralateral side of the facial midplane; and
processing the facial surface data and the mirrored nasal surface region to generate the nasal symmetry measure.

The nasal surface region may be laterally shifted to compensate for nasal deviation prior to generating the mirrored nasal surface region. The nasal surface region is user-defined. The nasal surface region may be an aesthetic subunit of the nose. A surface region associated with the aesthetic subunit may be automatically determined according to a pre-defined spatial region associated with the reference surface data. The nasal symmetry measure may be a single measure associated with the nasal surface region. A plurality of nasal surface measures may be generated for a respective plurality of nasal surface regions, each nasal surface region having a single associated nasal symmetry measure.

In some example implementations, the method further comprises:
employing a camera to obtain image data comprising the nose of the subject, the camera being rigidly mounted relative to the surface scanning device;
processing the image data such that the image data is represented in a common coordinate system with the transformed facial surface data; and
generating, within the common coordinate system, augmented reality annotation data associated with one or both of the nasal deviation measure and the nasal symmetry measure; and
generating and displaying an image comprising the image data and the augmented reality annotation data.

The augmented reality annotation data may comprise directional information indicating a direction suitable for correcting a local nasal deviation or local nasal asymmetry.

In some example implementations, the surface scanning device is a handheld surface scanning device.

In some example implementations, the facial surface data is acquired intraoperatively during a medical procedure, and wherein the nasal deviation and symmetry information is displayed intraoperatively during the medical procedure.

In another aspect, there is provided a system for assessing nasal deviation and symmetry, the system comprising:
a surface scanning device; and
control and processing circuitry operatively coupled to said surface scanning device, said control and processing circuitry comprising at least one processor and associated memory, said memory comprising instructions executable by said at least one processor for performing operations comprising:
controlling said surface scanning device to acquire facial surface data of a facial region of a subject, the facial region including a nose of the subject;
processing the facial surface data to determine a nasal deviation measure indicative of a lateral deviation between a nasal midline of the subject and a facial midplane of the subject;
processing the facial surface data to determine a nasal symmetry measure indicative of a degree of symmetry associated with a nasal surface region relative to the facial midplane; and
generating a display comprising nasal deviation and symmetry information, the nasal deviation and symmetry information being generated based on both the nasal deviation measure and the nasal symmetry measure.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 4A and 4B illustrate an example method of determining a nasal deviation measure.

FIGS. 5A and 5B show example images displaying a nasal deviation curve.

FIGS. 8A-8C: 2 mm of lateral deviation with less curvature (exponent n=3). FIGS. 8D-8F: 5 mm of lateral deviation with a higher curvature (exponent n=5).

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As noted above, a key outcome in craniofacial reconstruction is achieving symmetry, which is especially evident in rhinoplasty and nasal reconstruction. Achieving symmetry with high accuracy is critical for reducing surgical revision rates because a satisfactory outcome can depend on a discrepancy of millimeters. Conventional methods for assessing nasal asymmetry are challenging, both pre- and intra-operatively, when based on only a surgeons' visual perception, yet adjustments made of small distances (<2-3 mm) are important to cosmesis and function.

Figure 1:
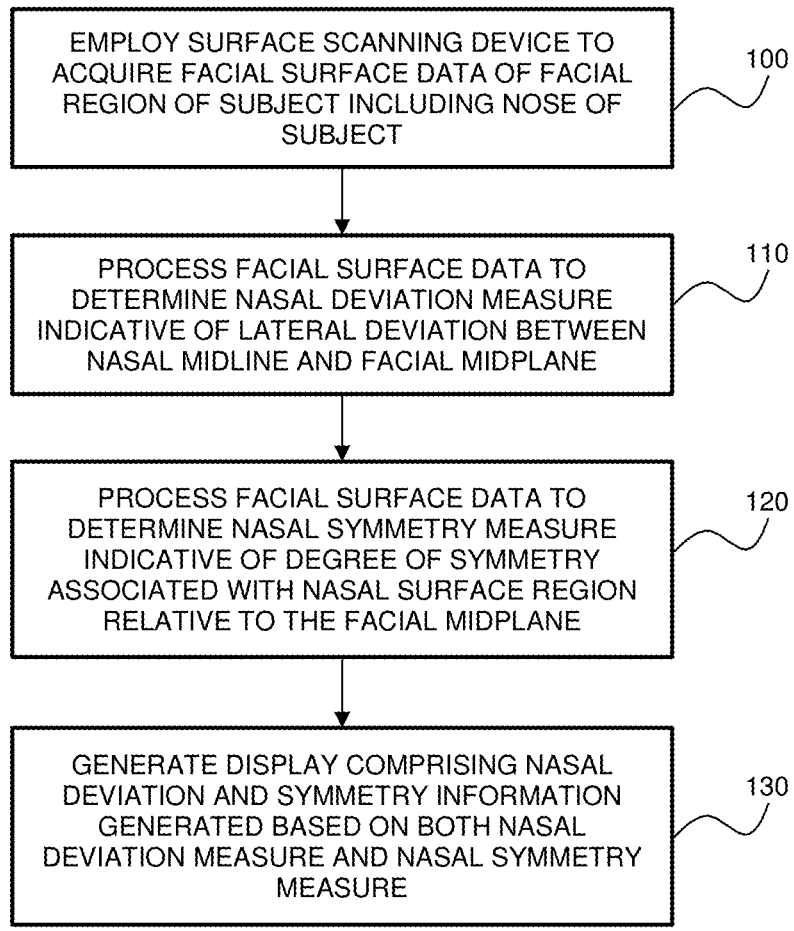
FIG. 1 is a flow chart illustrating an example method of performing an assessment of nasal deviation and symmetry.

The present inventors realized that improved intraoperative nasal assessment could be achieved using surface scanning of a facial region to generate combined measures involving both nasal deviation from the facial midline (midplane) and nasal symmetry. Referring now to FIG. 1, a flow chart is provided illustrating an example method of assessing nasal deviation and symmetry. As shown at 100, a surface scanning device is employed to acquire facial surface data of a facial region of a subject. The facial region may include, for example, selected facial regions that assist in the determination of a suitable facial midplane. For example, in some implementations, the scanned facial region may include the maxilla-mandibular region.

The facial region includes a nose of the subject and can include additional facial features that permit identification of a facial midplane (midline). At 110, the facial surface data is processed to determine a nasal deviation measure that is indicative of a lateral deviation between a nasal midline of the subject and a facial midplane of the subject. Examples methods of determining nasal deviation measures are described in detail below.

At 120, the facial surface data is also processed to determine a nasal symmetry measure indicative of a degree of symmetry associated with a nasal surface region relative to the facial midplane. The nasal symmetry measure provides, for example, a qualitative or quantitative determination of symmetry of a subregion of the nose, relative to a corresponding contralateral region. Example methods of generating such nasal symmetry measures are described in detail below.

Having generated the nasal deviation and nasal symmetry measures, nasal deviation and symmetry information, incorporating both measures, may be presented to a user, for example, via a user interface. Various example methods of presenting the nasal deviation and symmetry information are described in detail below. As described below, in some example implementations, the nasal deviation and symmetry may be presented as augmented reality annotations that are spatial registered with image data collected with a camera.

Figure 2A:
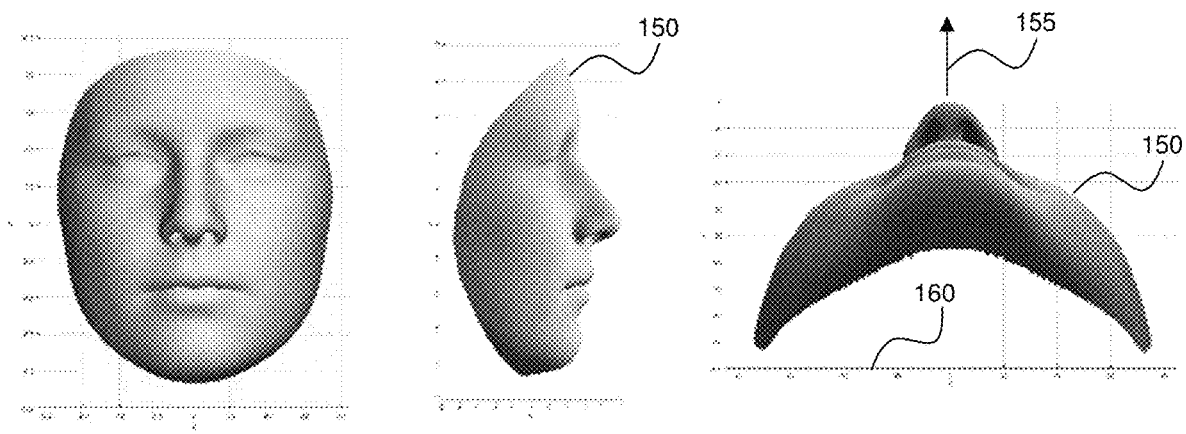
FIG. 2A illustrates example reference surface data characterizing a reference symmetrical facial shape and having a facial direction, in a direction perpendicular to a coronal plane, aligned with a selected coordinate system.
Figure 2B:
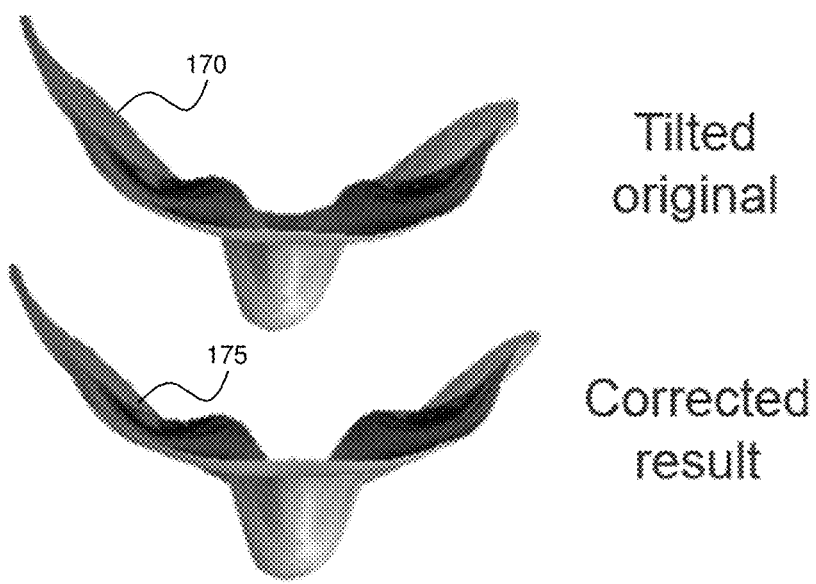
FIG. 2B illustrates the alignment of facial surface data to the reference surface data via image registration.

In some example implementations, prior to determining the nasal deviation measure and the nasal symmetry measure, surface registration is performed to register the facial surface data with reference surface data characterizing a reference symmetrical facial shape (e.g. based on atlas data). As shown in FIG. 2A, the reference surface data 150 may have a facial direction 155, in a direction perpendicular to a coronal plane, that is aligned with a selected coordinate system 160. According, after surface registration of the facial surface data 170, the transformed facial surface data 175 is aligned with the selected coordinate system. A facial midplane may be provided or generated based on the reference surface data 150. The surface registration may be performed according to many different known methods, such as, for example, an iterative closed point algorithm. In the event that a triangulated mesh is used to represent the facial surface data, the transformed facial surface data can be re-meshed on a rectilinear grid for simplifying transverse plane measurements. By registering the facial surface data to a symmetrical atlas with pre-existing alignment to the orthogonal planes, the midline and median plane of the scanned face is also an overall closest alignment to the orthogonal planes.

Figure 2C:
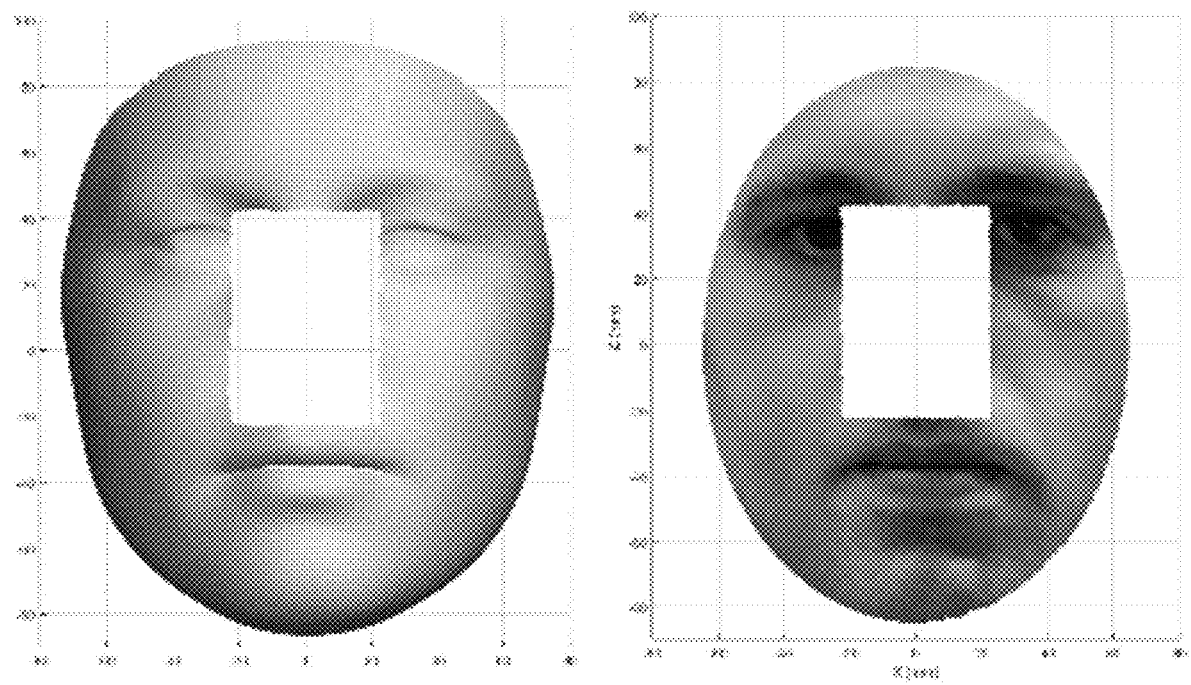
FIG. 2C illustrates the subtraction of surface data pertaining to the nose prior to image registration for improved registration quality.

In some example embodiments, prior to registering the facial surface data with the reference surface data, surface data from the nasal region may be removed (cropped out) to prevent or avoid nasal deviations from influencing the registration result, as shown in FIG. 2C (the nasal surface data may be removed from either or both of the facial surface data and the reference surface data). This step may improve the registration quality and alignment of the surfaces. The deviation measurements of the nasal and the maxilla-mandibular region midline can be assessed from the registered scan as the lateral distance away from the facial median plane.

As noted above, many different example methods may be employed to determine the nasal deviation measure. In some example embodiments, the nasal deviation measure may be determined based on the lateral offset from the maximal dorsal extension of the nasal surface data, as determined, for example, in a lateral direction within a transverse plane.

The present inventors realized, however, that such a method can be susceptible to errors and can yield inaccurate midline fluctuations, especially along the dorsum. The mathematical maximum projection for a subject's 3D nose shape may not represent the nasal midline because of variable skin curvatures (e.g. an off-center pimple or mole protruding farther than the dorsum or the nose tip). As well, in the exaggerated case of a perfectly flat dorsum, the mathematical maximum projection would be equal at both nasal lateral side walls and not in the middle of the dorsum.

Instead, the present inventors conceived of an improved algorithm for estimating the location of the maximal dorsal projection within a given transverse plane. By evaluating the nasal midline by using mid-point intersections from a small (e.g. 1-2 mm, 1-3 mm, 1-5 mm distance) behind the nasal surface, the midline is not simply located at the local maximum projection of the nose and provides a more accurate estimate. Accordingly, an example method for estimating the maximal dorsal projection was developed that employs line-curve intersections near the maximum projection (or minimum projection depending on the orientation) at each transverse plane.

Figure 3:
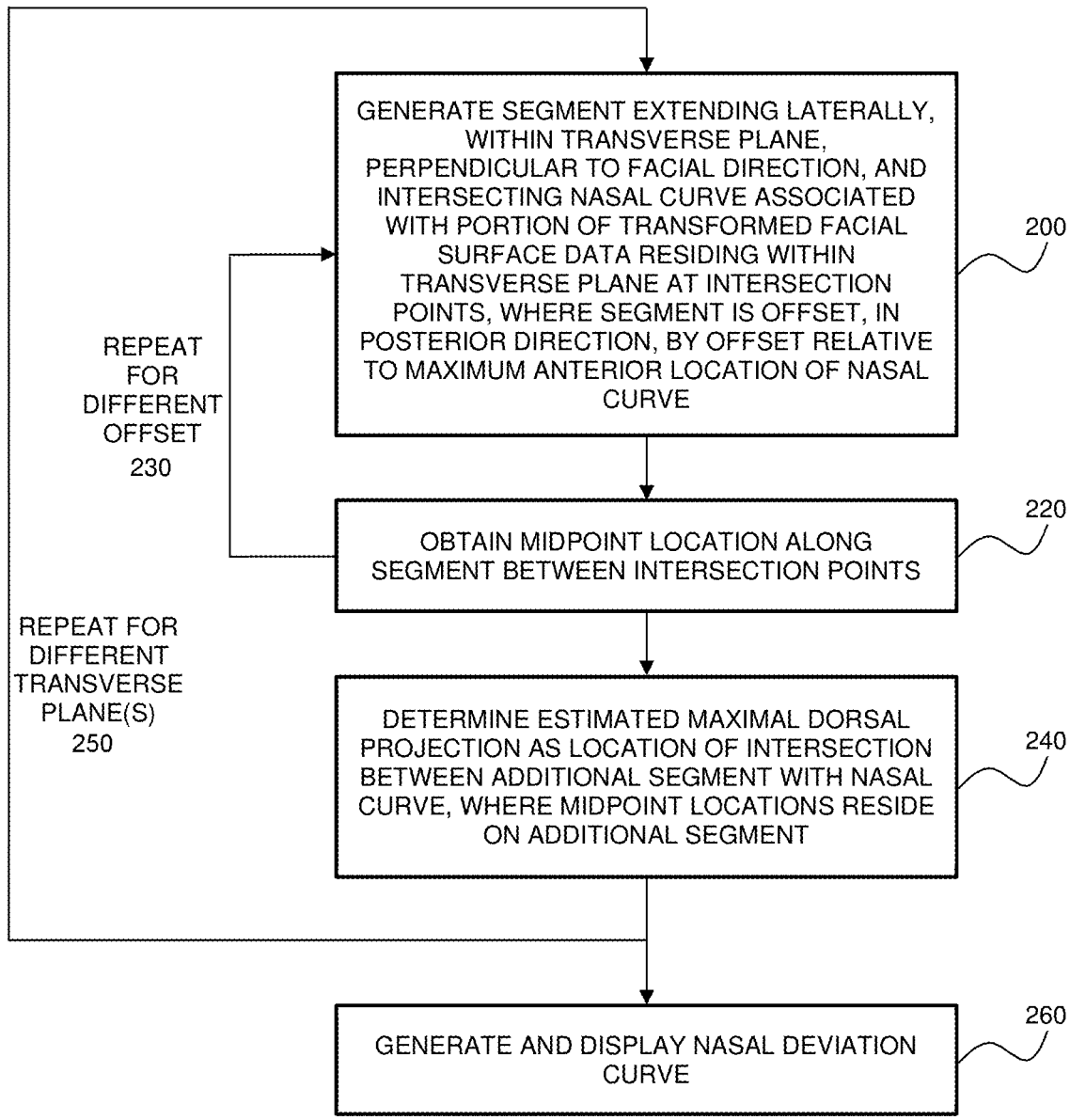
FIG. 3 is a flow chart illustrating an example method of determining a nasal deviation measure.

An example of such an algorithm is illustrated in the flow chart shown in FIG. 3 and the images shown in FIGS. 4A and 4B. FIG. 4A shows a transverse slice through the facial surface data in the nasal region. As shown in FIG. 4B, and step 200 of FIG. 3, a segment 270 is generated that extends laterally, within the transverse plane, perpendicular to the facial direction, and intersects a nasal curve 280 associated with the portion of the transformed facial surface data residing within the transverse plane at first intersection points. The segment is being offset, in a posterior direction, by an offset relative to a maximum anterior location of the nasal curve. A midpoint location along the segment between the intersection points is then found, as shown at 220 in FIG. 3. The process is then repeated, as shown at 230 in FIG. 3, to generate another segment 275 and associated midpoint, at a different posterior offset. In some example implementations, the offsets may range, for example, between 1 to 2, 1 to 3, 1 to 4 and 1 to 5 mm. As shown in FIG. 4B and step 240 of FIG. 3, the estimated maximal dorsal projection 290 for the given transverse plane may be determined as the location of intersection between an additional segment 280 with the nasal curve, where the midpoint locations reside on the third segment. The nasal deviation may then be determined based on the lateral offset between the estimated maximal dorsal projection and the facial midplane.

As shown in step 250 of FIG. 3, this process may be repeated for a plurality of nasal deviation measure comprises a plurality of nasal deviations (lateral differences), each nasal deviation being determined within a separate transverse plane. A nasal midline curve may be generated based on the plurality of nasal deviations corresponding to the different transverse planes. FIGS. 5A and 5B illustrate the display of a nasal midline curve and associated nasal deviation from the facial midplane according to colour.

In another example embodiment, the nasal deviation (nasal midline) may be found by deformably registering a face mesh with a known midline to measure the new three-dimensional coordinates of that midline on the morphed patient-specific face shape.

Figure 6A:
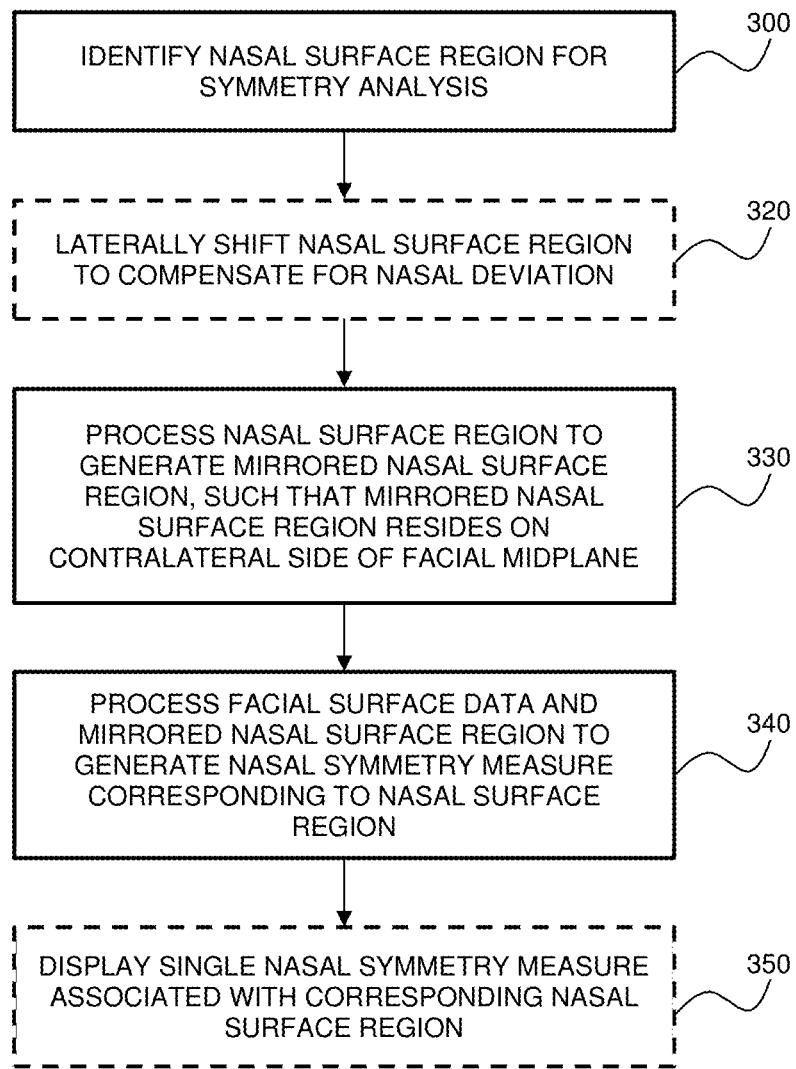
FIG. 6A is a flow chart illustrating an example method of performing assessment of nasal symmetry.

Referring now to FIG. 6A, a flow chart is provided illustrating an example method of generating a nasal symmetry measure. In step 300, a nasal surface region (subregion of the nose) is initially identified or determined. As shown at step 330, the surface data within the nasal surface region maybe processed to generate a mirrored nasal surface region that resides on a contralateral side of the facial midplane. This mirrored nasal surface region may then be compared to the unmirrored facial surface data to generate the nasal symmetry measure, as shown at step 340, for example, based on concurrency or the average distance between the surfaces. For example, a RMS difference between the two surfaces may be employed to generate a suitable symmetry measure. Alternatively, a measure of surface-to-surface registration quality may be employed to generate a symmetry measure.

As shown at optional step 320 of FIG. 6A, nasal surface region may be laterally shifted to compensate for nasal deviation prior to generating the mirrored nasal surface region.

In some example embodiments, a single nasal symmetry measure may be calculated and shown associated with the nasal surface region, as shown at step 350. Furthermore, a plurality of nasal surface measures may be generated for a respective plurality of nasal surface regions, with each nasal surface region having a single associated nasal symmetry measure.

Whereas previous facial symmetry analysis measure distance to a 3D mirror image, the deviation results are conventionally presented as a full 3D facial surface with a color spectrum representing deviation value, which can be challenging for a clinician to interpret. The present example embodiment nasal self-symmetry measuring algorithm may include labelled regions (aesthetic subunits) to enable presenting the deviation results as a single average or root-mean-square value per subunit region for improved clinical understanding and applicability.

In some example embodiments, the per-subunit deviation measurement may also be presented with directional guidance to provide arrows indicating the adjustment direction needed from a deviated nose to a corrected position. The regional values and directional guidance are especially valuable for a clinician in making small adjustments (in the range of less than 3 mm) where perception of distance can be limited.

The nasal aesthetic subunit regions could be labels algorithmically or, alternatively, selected manually by the clinician as a region of interest. For example, the nasal surface region may be identified by a user via a user interface. Alternatively, a suitable nasal surface region may be automatically determined. The nasal surface region may be an aesthetic subunit having a known location within the reference surface data (atlas data), enabling the automated determination of its location within the facial surface data transformed into the coordinate system of the reference surface data, for example, via deformable registration. Also, nasal subunit regions may be labelled for average nose shapes depending on a subjects' age, sex, race, body-mass index (BMI)—for example, a different labelling & 3D reference surface data would likely be need for an infant's nose with cleft palate than for an adult nose with skin cancer.

An alternative approach to subunit locating on the measured face can potentially be done by a curvature analysis with region location determined relative to the nose tip.

In addition to analyzing averages for subunit regions, deviation values at specific nasal points can also be user-selected by the clinician.

Figure 6B:
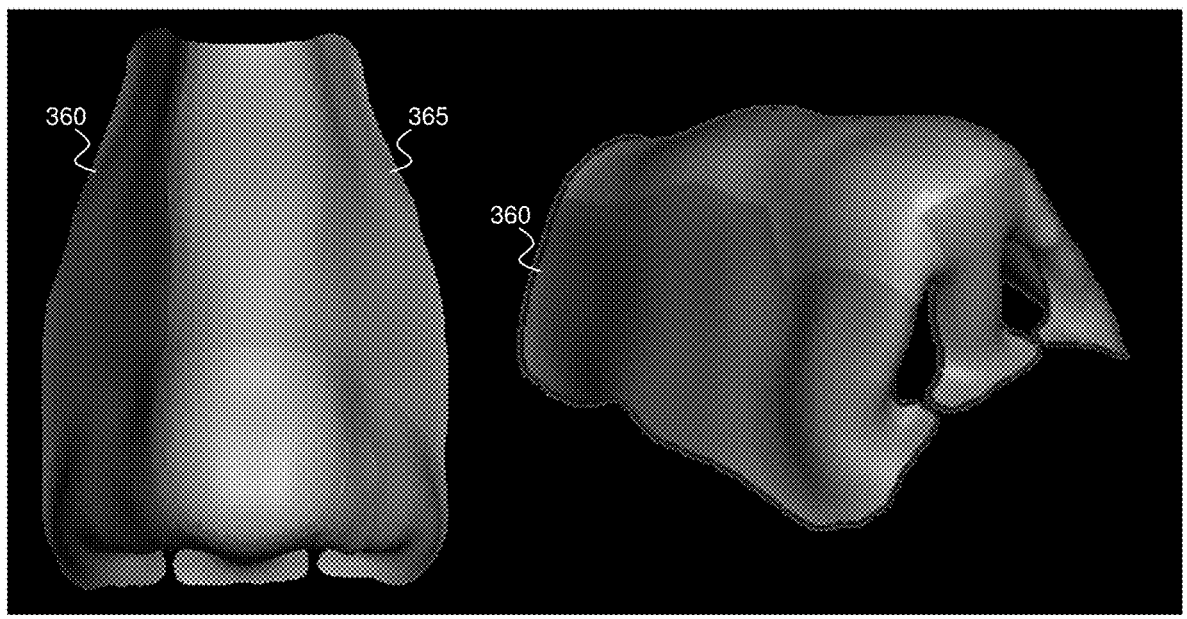
FIG. 6B shows an example of a nasal surface with a nasal region selected for the determination of a nasal symmetry measure.
Figure 6C:
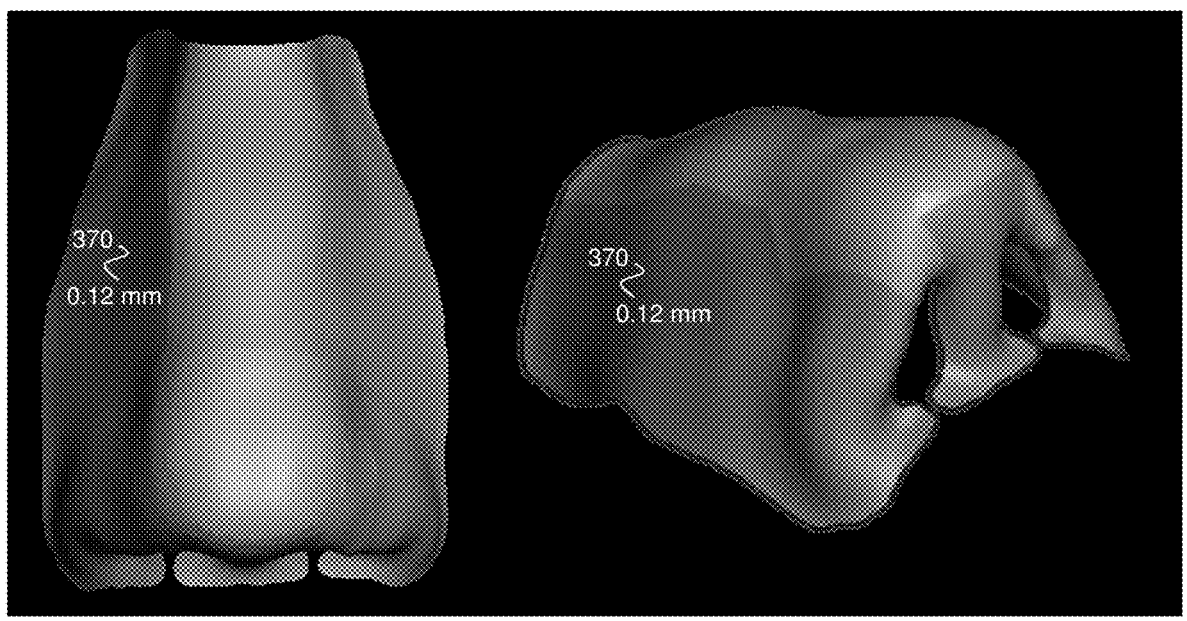
FIG. 6C shows an example of a nasal surface with a selected nasal region annotated with a calculated nasal symmetry measure.
Figure 7:
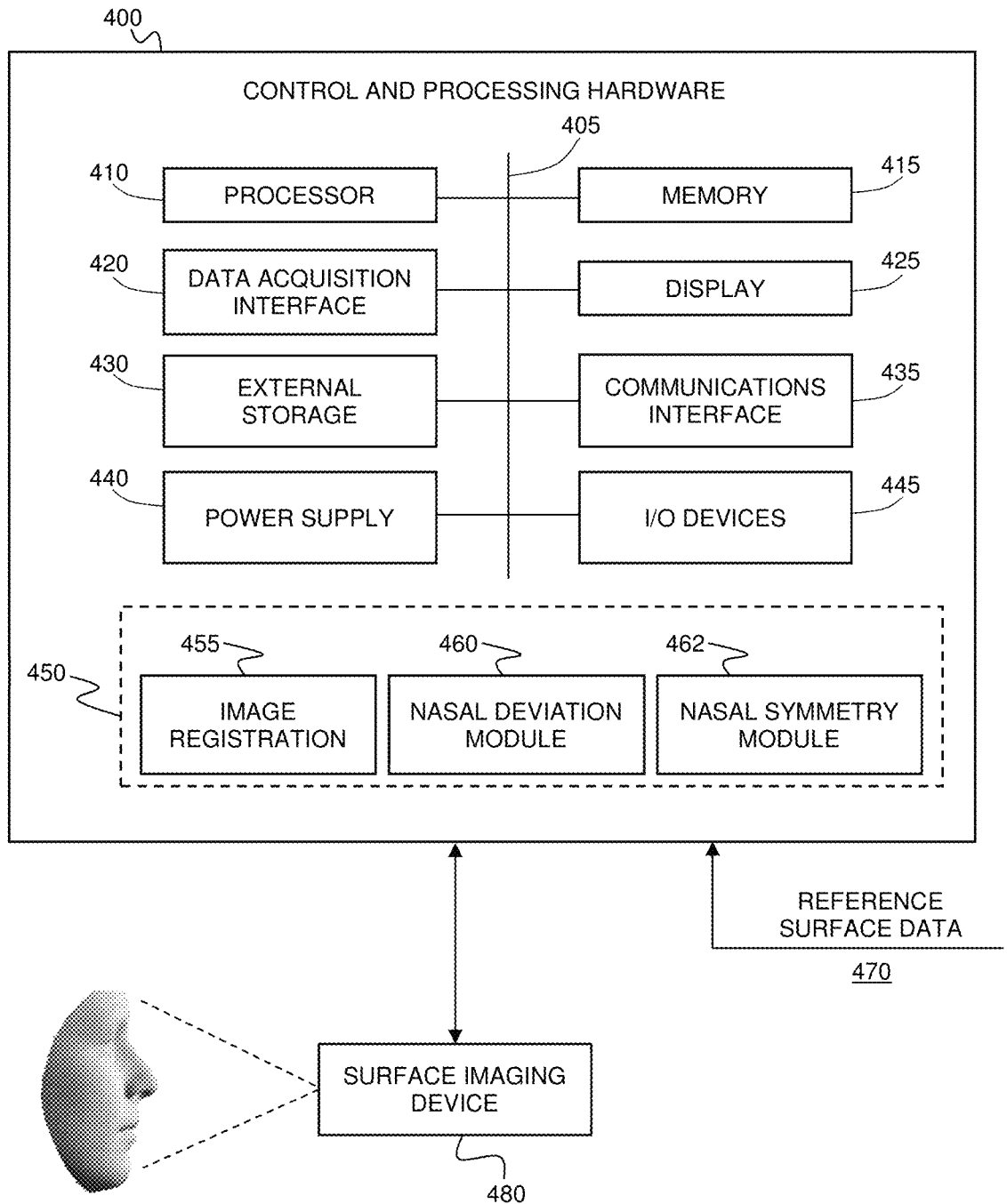
FIG. 7 shows an example system for assessing nasal deviation and symmetry.
Figure 8A:
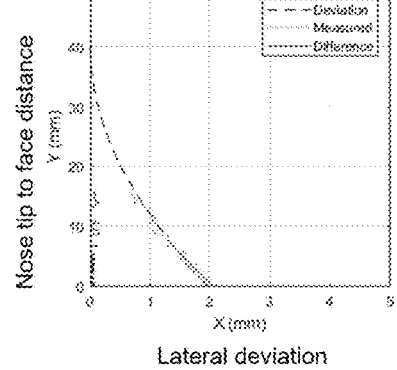
FIGS. 8A-8F show results from an asymmetrical nose model with variable twist.
Figure 8B:
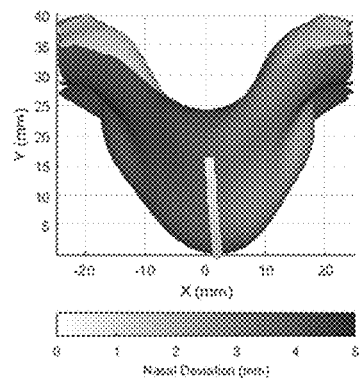
Figure 8C:
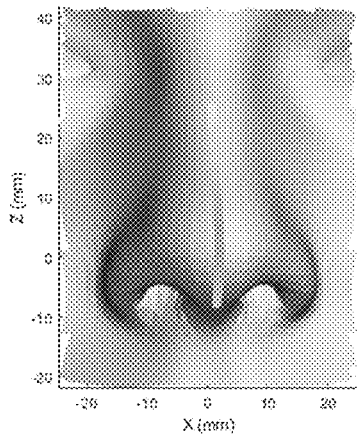
Figure 8D:
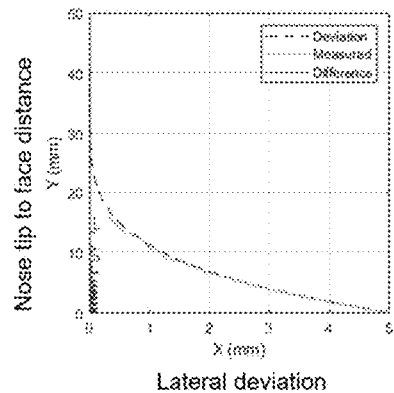
Figure 8E:
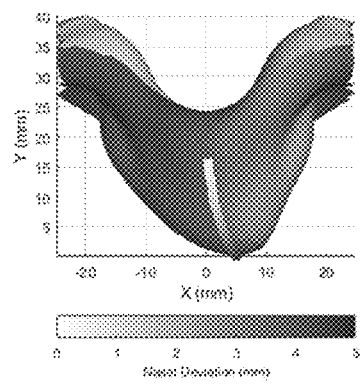
Figure 8F:
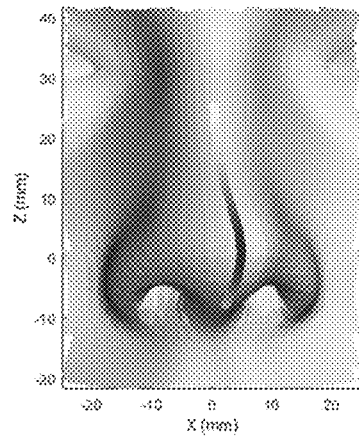
Figure 9:
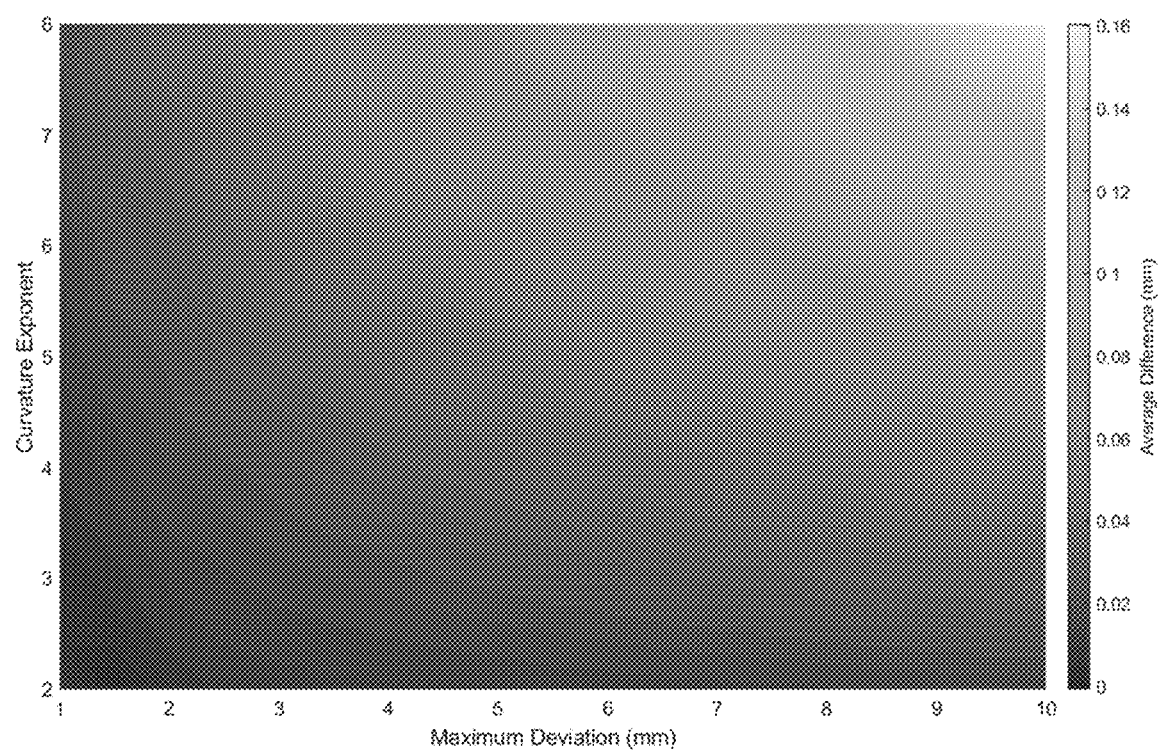
FIG. 9 plots the process parameter map measuring the average difference between the model and the measured result for increasing lateral deviation and increasing twist exponent.

It will be understood that the nasal deviation and symmetry information may be presented according to a wide variety of formats. For example, the lateral deviation data may be presented as a 3D deviation path along the nose that is visualized with the distances mapped with color or arrows according to the magnitude at the deviation midline location. In some example implementations, the deviation distance value along the nose can be measured and presented at specific points, for example, at the maximum, average, at the nose tip (maximum projection), at the radix (top of the nose). In some example implementations, the distances compared to the contralateral side for a mirrored nose can be labelled according to each aesthetic subunit with coloring or arrows representing the deviation distance. An example of such an embodiment is illustrated in FIGS. 6B and 6C, where FIG. 6B shows a selected aesthetic subunit 360, and its contralateral region 365, and FIG. 6C shows an example distance offset annotation 370 associated with the selected aesthetic subunit.

In some example implementations, the nasal deviation and symmetry information may be presented as augmented reality annotations overlaid on an image of the subject's face. For example, a camera may be employed to obtain image data comprising the nose of the subject, with the camera being rigidly mounted relative to the surface scanning device. The image data may be processed such that the image data is represented in a common coordinate system with the transformed facial surface data. Augmented reality annotation data associated with one or both of the nasal deviation measure and the nasal symmetry measure may then be generating within the common coordinate system. An image including the image data and the augmented reality annotation data may then be generated and presented. The augmented reality annotation data may include directional information indicating a direction suitable for correcting a local nasal deviation or local nasal asymmetry.

In some example implementations, the facial surface data may be acquired preoperatively, and/or intraoperatively during a medical procedure, and/or post-operatively.

The present example nasal measurement algorithms based on surface data may provide an improved measuring tool for pre-operative and on-table assessments with the aim of ensuring optimal patient outcomes, reducing surgery time, and re-operation rates in nasal surgery. The described measurement algorithm quantifies deviation along the dorsum and nasal tip from facial 3D scan data, with visualization of the 3D path of the deviating midline illustrating how and where the maximum deviation is located on the nose. By better localizing deviations within the nose, a pre-operative analysis can assist the surgeon in planning their correction, for example, by determining if osteotomies are required to correct a bony vault asymmetry or whether the perceived asymmetry is confined to the middle cartilaginous vault.

FIG. 6 provides a block diagram illustrating an example implementation of a system for performing diagnostic or therapeutic transcranial procedures. Control and processing hardware 400 is operably connected to a surface detection device 480. A surface scanning device may employ, for example, a modality such as structured light or stereo-photogrammetry. In structured light 3D scanning, a known pattern is projected (in the visible or infra-red spectrum) on an object and the distortion of the pattern is visualized with a camera to calculate the object shape. In stereo-photogrammetry, points on a 3D surface are calculated in space from multiple 2D photos taken at different locations and angles around an object. Examples of commercially available clinical stereo-photogrammetry 3D scanners include the Vectra M3 (Canfield Scientific, NJ) and the 3DMD-Face (3D MD Systems, GA). The Kinect (Microsoft, released 2010) first made infra-red structured light 3D scanners commercially available to the mass market as a gaming system accessory. This infra-red 3D scanning technology has more recently been miniaturized into mobile applications. The iPhone X (Apple, released 2017) has popularized the hardware to enable 'FaceID' with its TrueDepth camera system, where >30,000 dots are projected an arm's length away from the face (25-50 cm) and captured by an infra-red camera. The Pixel 4 (Google—Alphabet, released 2019) has also incorporated this type of sensor to enable its 'Face Unlock' feature. Software applications, such as FaceApp (Bellus3D, CA), are available to the millions of people with these mobile devices, democratizing the ability to capture 3D 'selfies'. Similar miniaturized infra-red 3D scanning technology has also been developed into stand-alone devices, such as the Structure Sensor (Occipital, CO) and the Arc Scanner (Bellus3D, CA). The control and processing hardware 400, which includes one or more processors 410 (for example, a CPU/microprocessor), bus 405, memory 415, which may include random access memory (RAM) and/or read only memory (ROM), a data acquisition interface 420, a display 425, external storage 430, one more communications interfaces 435, a power supply 440, and one or more input/output devices and/or interfaces 445 (e.g. a speaker, a user input device, such as a keyboard, a keypad, a mouse, a position tracked stylus, a position tracked probe, a foot switch, and/or a microphone for capturing speech commands).

Reference surface data 470, which characterizes a reference symmetrical facial shape and has known facial direction (orientation) aligned with a known coordinate system, may be stored on an external database or stored in memory 415 or storage 430 of control and processing hardware 400.

The control and processing hardware 400 may be programmed with programs, subroutines, applications or modules 450, which include executable instructions, which when executed by the one or more processors 410, causes the system to perform one or more methods described in the present disclosure. Such instructions may be stored, for example, in memory 415 and/or other storage. The control and processing circuitry 400 includes executable instructions for controlling the surface detection system 480 to acquire facial surface data from the facial region of a subject and processing the facial surface data to determine the nasal deviation and nasal symmetry measures. The image registration module 455 may be employed for registering the acquired facial surface data to the reference surface data 470. The nasal deviation module 460 includes executable instructions for determining a nasal deviation measure, for example, according to the example algorithms disclosed above. The nasal symmetry module 462 includes executable instructions for determining a nasal symmetry measure, for example, according to the example algorithms disclosed above.

Although only one of each component is illustrated in FIG. 6, any number of each component can be included in the control and processing hardware 400. For example, a computer typically contains a number of different data storage media. Furthermore, although bus 405 is depicted as a single connection between all of the components, it will be appreciated that the bus 405 may represent one or more circuits, devices or communication channels which link two or more of the components. For example, in personal computers, bus 405 often includes or is a motherboard. Control and processing hardware 400 may include many more or less components than those shown.

The control and processing hardware 400 may be implemented as one or more physical devices that are coupled to processor 410 through one of more communications channels or interfaces. For example, control and processing hardware 400 can be implemented using application specific integrated circuits (ASICs). Alternatively, control and processing hardware 400 can be implemented as a combination of hardware and software, where the software is loaded into the processor from the memory or over a network connection.

Some aspects of the present disclosure can be embodied, at least in part, in software, which, when executed on a computing system, transforms a computing system into a specialty-purpose computing system that is capable of performing the methods disclosed herein. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Validation Using Modelled Asymmetrical Noses

A digital model with a known nasal asymmetry was developed to test the example nasal deviation measuring algorithm. To simulate a patient in need of rhinoplasty, a 3D nose was first cropped from the 'average face' generated from the large-scale facial model and mirrored for perfect symmetry. The nose morphology was then converted from a random triangular mesh to a gridded square surface to enable analysis along orthogonal planes. An exponential curve ($y=Ax^n$) was applied to twist the nose laterally without affecting the facial geometry. The adjustment factor (A) was set to control the maximum lateral deviation and the exponent (n) to control the curvature, where the larger the exponent, the sharper the twist.

The measuring algorithm for lateral deviation was tested by calculating the average difference between the intended and measured midline deformation in the nose model, with the assessment independent of the model's twist parameters. The maximum lateral deviation and curvature parameters were varied to evaluate and map the measurement's average difference up to exaggerated simulated values (10 mm lateral displacement). The midline is plotted on the 3D nasal surface with distance color-mapping to better enable visualization of its deviation magnitudes.

In the simulated deviation model, the exponential function to adjust curvature was applied to the average nose and two examples of the resulting asymmetrical nose are presented in FIGS. 8A-8F. The FIGS. 8A-8C demonstrate a small lateral deviation with a low curvature (2 mm, n=2) and FIGS. 8D-8F demonstrate a larger lateral deviation with higher curvature (5 mm, n=5). The lateral deformation applied to the average nose (blue dashed line) increases anteriorly as the nose projects farther from the face.

The modelled asymmetry is best visualized in the horizontal plane (bird's eye view) as the lateral deviation is more challenging to perceive from the front view without the measurement. With the midline measurement algorithm applied blind to the model nose shape parameters, the 3D path of the deviating midline is highlighted along the nose's dorsum and tip regions, and a scaled colormap indicates the amount of lateral deviation. The measured nasal midline lateral deviation (light grey line) was compared to the applied deformation and the difference between them (dark grey line) calculated. For the model examples illustrated, the average difference between the measured and calculated deviation was ~0.01 mm (10 µm) for the nose with the small asymmetry and was ~0.04 mm (40 µm) for the nose with the larger asymmetry.

Lateral deviation and curvature were varied to explore the effect of all parameter combinations on the average difference error using the measurement algorithm on the asymmetrical nose model. On the parameter map (FIG. 5.4), the average difference between the intended and measured deformation was found to range from 0.02-0.06 mm (20-60 µm) in models combining lower curvature (n: 2-5) and smaller lateral deviations (1-5 mm). For more exaggerated curvatures (n: 6-8) and larger lateral deviations (6-10 mm), the average difference measured increased up to 0.16 mm (160 µm). The average difference error increased with larger curvatures and deviations because the true midline deviated farther from measurement between the 1 mm posteriorly behind it where the midpoint is calculated.

Example 2: Benefits of Nasal Midline Measurement

Figure 10A:
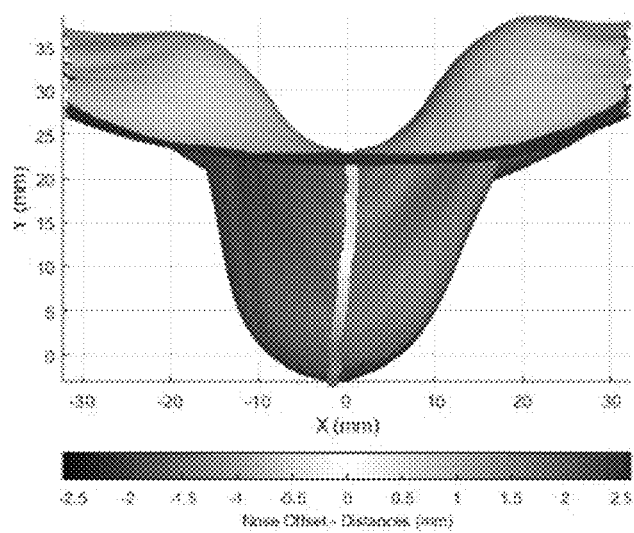
FIGS. 10A-10C show an example implementation of the determination of the nasal midline.

The nasal midline measuring algorithm provides a lateral deviation assessment with a 3D pathline varying all along the dorsum and nose tip regions, as shown in FIG. 10A. The coloring of this midline result can correlate to the magnitude of the lateral deviation, with a color scale to better visually represent the data to the clinician, such that low deviation values are distinct from high deviation values.

Figure 10B:
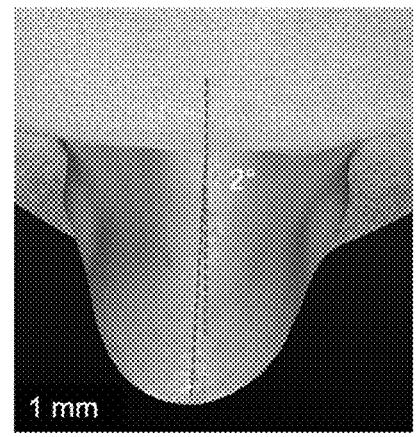

The midline measurement all along the dorsum and tip regions is in contrast to existing techniques in practice (FIG. 10B), where a distance and/or angle is measured only to the nose tip outermost maximal projection point as a straight line from the facial median plane. By measuring the local midline all along the nose, the deviation better evaluates patients where the maximum deviation is not necessarily located at the outermost projection, for example with a 'C-shaped' nose.

Figure 10C:
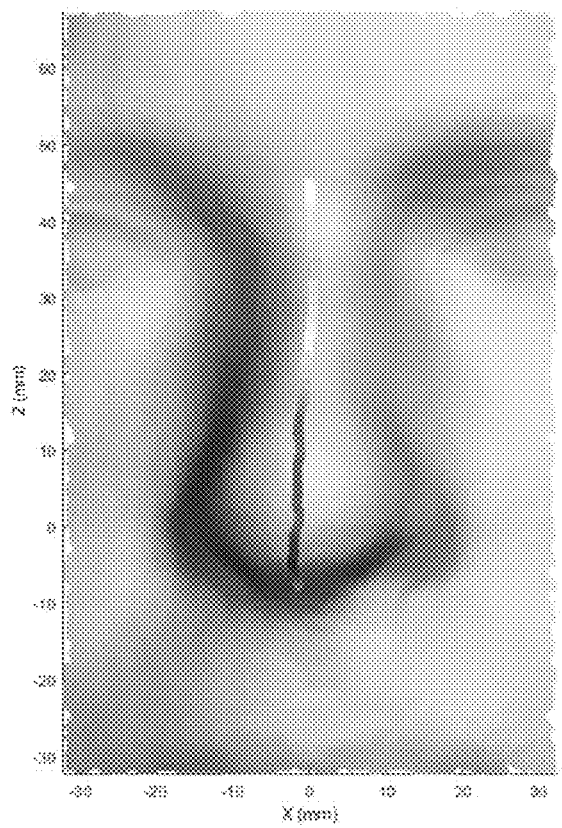

Extending the deviation measurement and midline path beyond the nose tip region (FIG. 10C) also enables the clinician to just the nasal cartilage deviation relative to the position of the bony nasal vault and philtrum.

Example 3: Measuring Midline Deviation on Multiple Subjects

Figure 11:
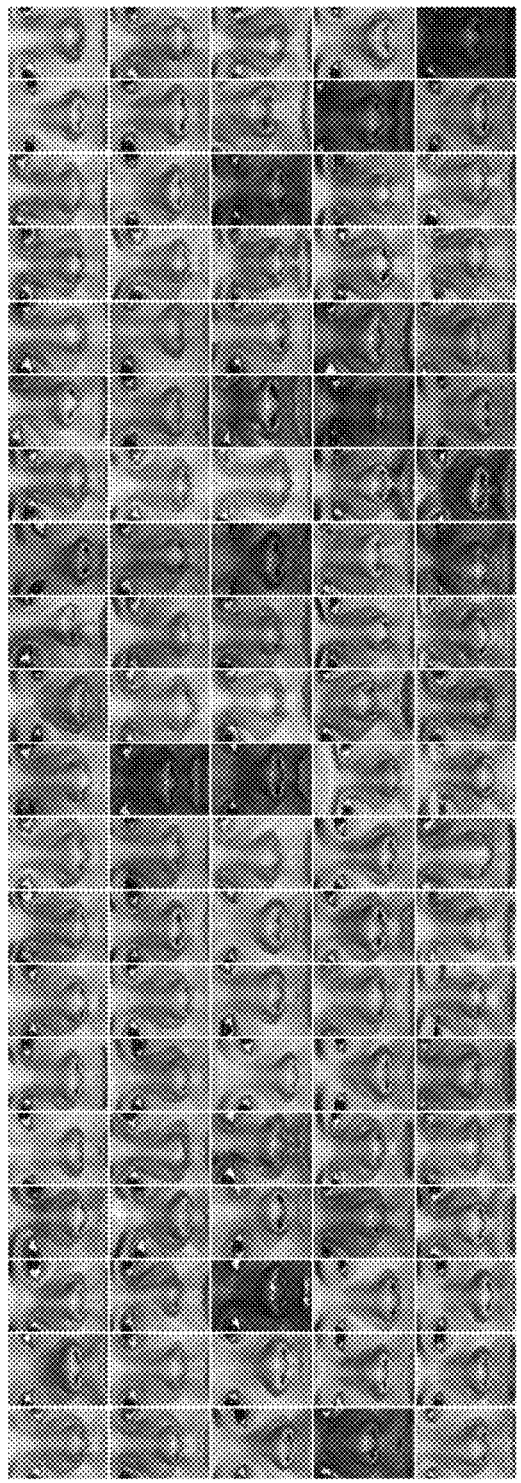
FIG. 11 shows a montage of 100 subjects' noses from BU-3DFE database front-view photos.

The deviation measurement algorithm was then evaluated on a collection of 3D face scans from 100 subjects in the Binghamton University 3D Facial Expression (BU-3DFE) database. The subjects consist of 56 females and 44 males, with multi-racial grouping identified as: White/Caucasian (51), East-Asian (24), Black/African (9), Latino-Hispanic (8), Indian/South-Asian (6), and Middle-East Asian (2). The analysis on these 3D faces was measured on subject scans with neutral expression. The noses cropped from the database are illustrated with a montage of front-view photos, shown in FIG. 11.

To measure a subject's nose, their 3D face scan was first aligned to the average face by the nasal tip and then rigidly registered with an iterative closed point algorithm to remove tilt relative to the orthogonal planes. This registration step was performed with the 3D nose cropped out of the scan so that the deviating noses did not affect the tilt correction. The facial midline was positioned at zero on the X-axis. The registration step was validated by comparing the facial surface to its own lateral mirror image, where the average distance for all 100 subjects was 1.34 mm across the whole face. The nose morphology data was then converted from a triangular mesh to a gridded surface to facilitate analysis of the contour shape along the orthogonal transverse planes. The nasal midline was evaluated across the height of the dorsum and the nose tip aesthetic subunits. For all subjects, the average maximum nasal deviation was calculated, as well as the average deviation across the dorsum, at the nose tip, and at the nasion. For the 100 subject sample size within the BU-3DFE database and a statistical power of 0.80, a 0.3 mm average difference is detectable. A correlation analysis was performed to determine if there was any relationship between the maximum lateral deviation data and nose size (measured from the pronasale point posteriorly to the face) to evaluate whether larger noses are more likely to deviate.

Figure 12:
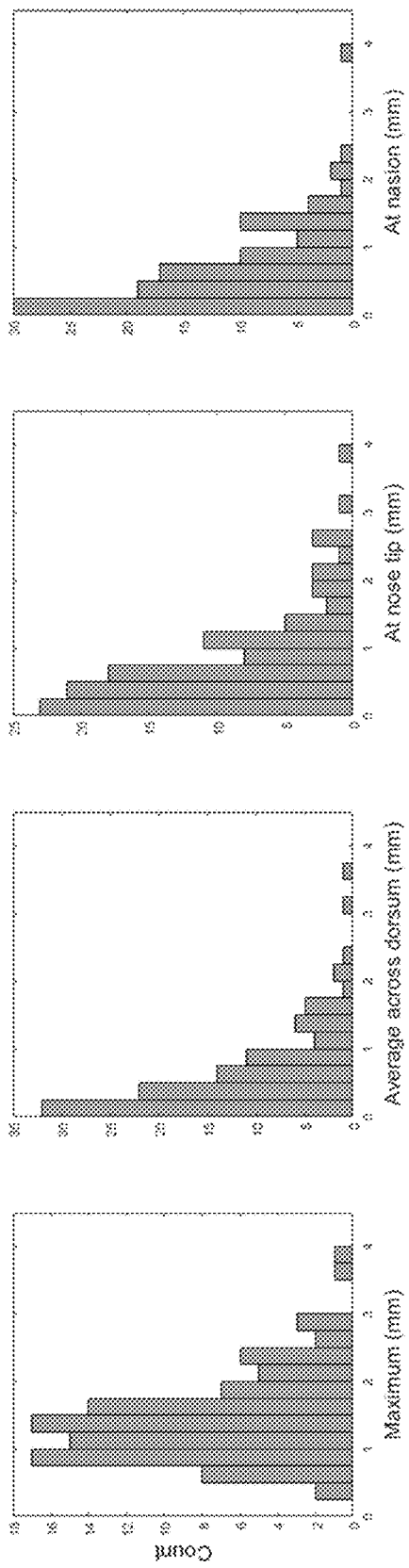
FIG. 12 shows histograms of nasal asymmetry measured on the 100 subjects of the BU-3DFE data set by mid-dorsum deviation (left to right): maximum, average across dorsum, at the nose tip, and at the nasion.

The measurement algorithm analysis was applied to all 100 subjects in the BU-3DFE database with the histograms presented for the absolute maximum lateral deviation, the average deviation across the dorsum, and deviation at the tip, as shown in FIG. 12. For all subjects, the average absolute maximum deviation was 1.5±0.76 mm (range: 0.49 to 4.4 mm). A cumulative distribution function of the subjects' maximum deviation measurements indicates that 96% of this population has less than 3.0 mm of asymmetry, corresponding to +2a. The absolute average for all subjects of the deviation was 0.66±0.68 mm along the midline (dorsum & tip) and 0.79±0.73 mm at the tip. The average nasal tip deviation (0.79 mm) was about half the average maximum (1.5 mm), highlighting that the maximum deviation along the nose often did not occur at the point of maximum projection, which in all cases was within the tip region. At the top of the dorsum, the average nasion deviates 0.68±0.64 mm and a cumulative distribution function of the subjects indicates that ~80% of subjects have less than 1.0 mm of asymmetry at the nasion.

Figure 13:
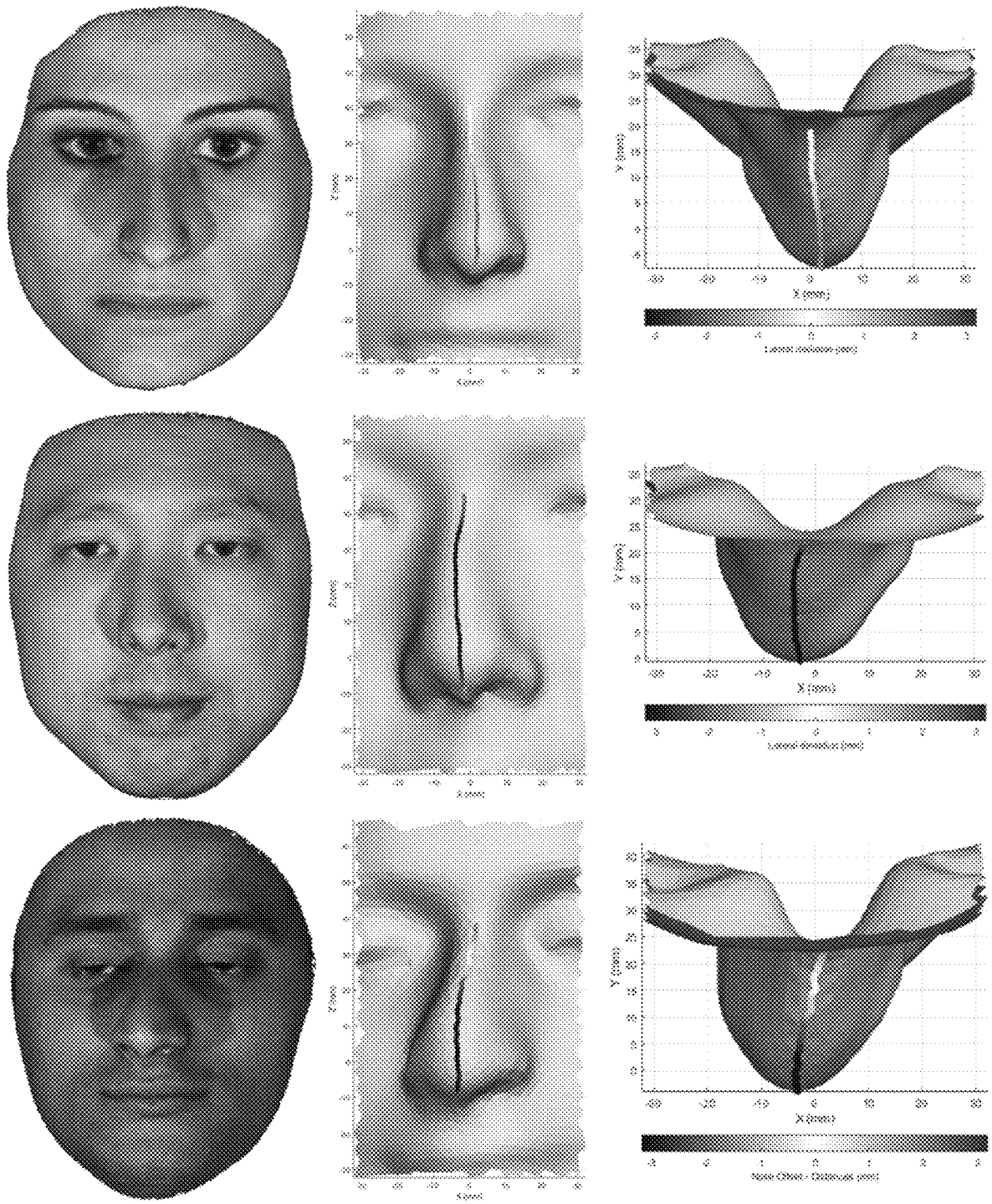
FIG. 13 shows midline dorsum & tip deflection measured on 3 subjects in the BU-3DFE database. Top: Female #10, middle: Male #25, & bottom: Male #37 deviations analyzed. For each subject, a 3D nose scan is presented with the midline traced and the lateral distance from the median plane indicated on an associated magnitude colormap (front and top view).

Measurements on three subjects from the BU-3DFE database are provided as examples of the analysis to highlight facial variability and the utility in such an analytic tool. Female #10 (FIG. 13, top, top) is presented as an example of I-shaped lateral deviation. The average deviation along her nasal midline (dorsum & tip) was 1.57±0.63 mm, with maximum deviation of 2.34 mm along the nose and 2.17 mm at the tip. This subject's maximum deviation was the 83rd highest within the BU-3DFE cohort and illustrates how the nasion can align with the endocanthion/mid-intercanthal point (evident from the white colored midline path at ~0 mm of deviation) with asymmetry confined to the lower mid-vault and tip. This case illustrates the value of the presented algorithm in confirming bony vault symmetry, which would have implications for the surgical planning when reconfiguring the bony vault.

Male #25 (FIG. 13, middle) is presented as an example of the largest deviation analyzed in the 3D scan database and represents a C-shaped deformity. The average deviation along this subject's nasal midline was −3.62±0.54 mm, with a maximum deviation of −4.35 mm along the nose and −3.04 mm at the tip. Male #25 represents asymmetry of nasal bone structure in addition to cartilaginous midline deviation, where the nasion does not align with the mid-intercanthal point. This offset carries through along the bony dorsum, cartilaginous dorsum, and tip, and the midline centers back towards the columella and mid-philtral point. This case illustrates the value of graphic analysis in the assessment of one of the more common nasal deformities by confirming deviation of all three structural zones of the nose, which may not be easily appreciated on simple inspection due to the inherent deviation within the nose from the nasal midline.

Male #37 (FIG. 13, bottom) is similarly presented as an example of overall facial asymmetry effecting the nasal deviation. The average along this subject's nasal midline was −1.40±1.42 mm, with a maximum deviation of −2.78 mm along the nose and −2.55 mm at the nasal tip. In this case, the nasal bone and orbit asymmetry causes the midline path to deviate on both sides of the face's medial plane, once again having implications for surgical planning in aligning the subject's nose with his facial midline. These subject specific analyses illustrate the value of a validated algorithm in delineating specific nasal asymmetries for surgical planning that are often complex and difficult to analyze on inspection alone.

Figure 14:
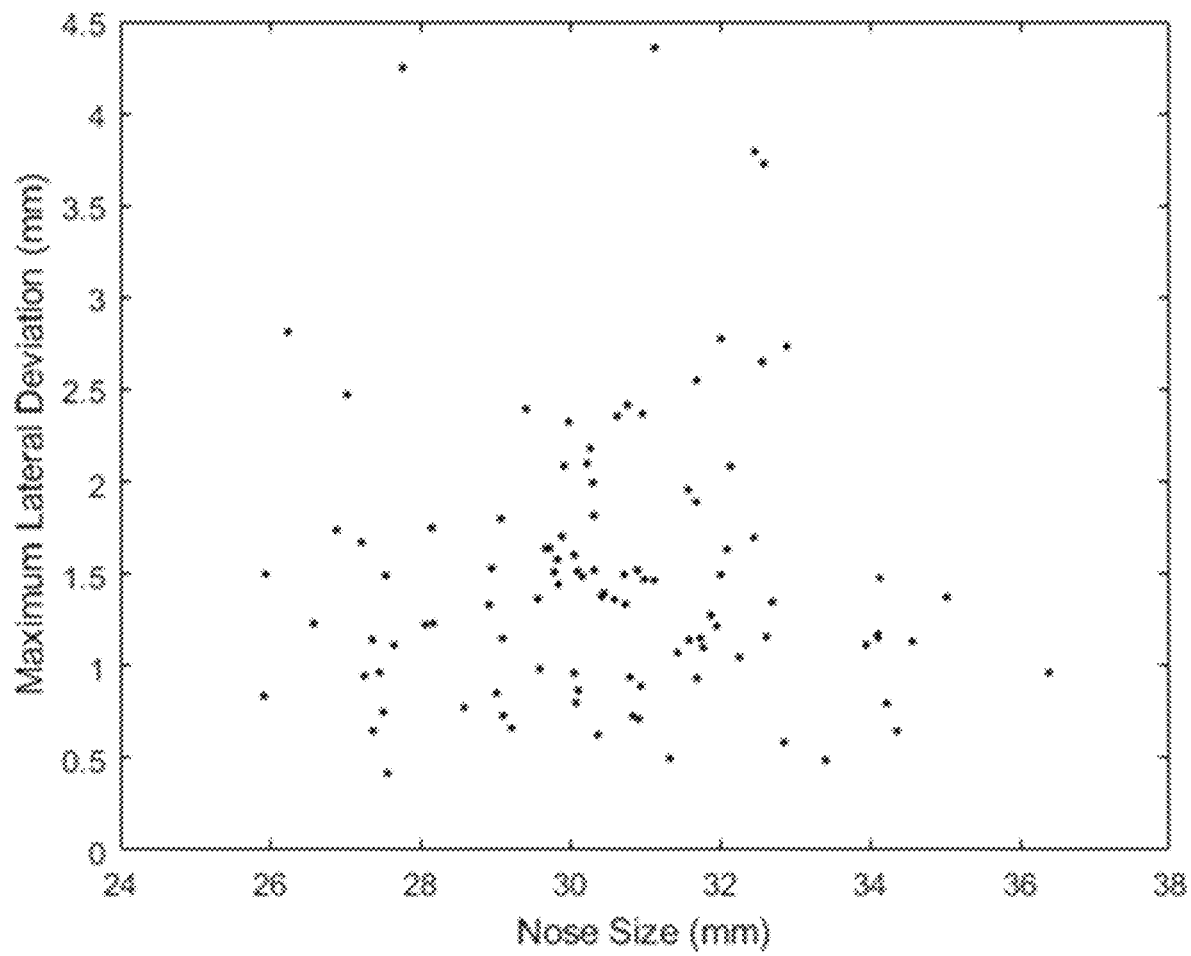
FIG. 14 shows that lack of correlation found between subjects' nose size and maximum lateral deviation

In comparing nose size to deviation measurements, no correlation was found with the maximum lateral deviation ($R^2$=0.000017, p=0.97, FIG. 14). The lack of correlation indicates large noses can be highly symmetrical and small noses can also be highly asymmetrical.

The development of an accurate nasal deviation measurement tool has the potential to improve rhinoplasty pre-operative planning through the quantification and delineation of nasal asymmetry. The measurement algorithm quantifies deviation along the dorsum and nasal tip from facial 3D scan data, with visualization of the 3D path of the deviating midline illustrating how and where the maximum deviation is located on the nose. Validation of the algorithm was accomplished in evaluating simulated 3D nasal asymmetries. In this, the difference between the deviation measurement and modelled nose was clinically negligible (20-60 µm).

Beyond the validation model, the analysis of 100 noses from the BU-3DFE database presents a clinical context with respect to nasal asymmetry, providing a baseline for the comparison of nasal asymmetry deviation in individual patients with this cohort. The symmetry analysis of these 100 subjects ensured that the deviation measuring algorithm can perform reliably for nose shapes encountered in a diverse patient population, demonstrated lack of any correlation between nose size and deviation and illustrated how such an analysis can help guide pre-operative analysis for surgical planning.

Figure 15A:
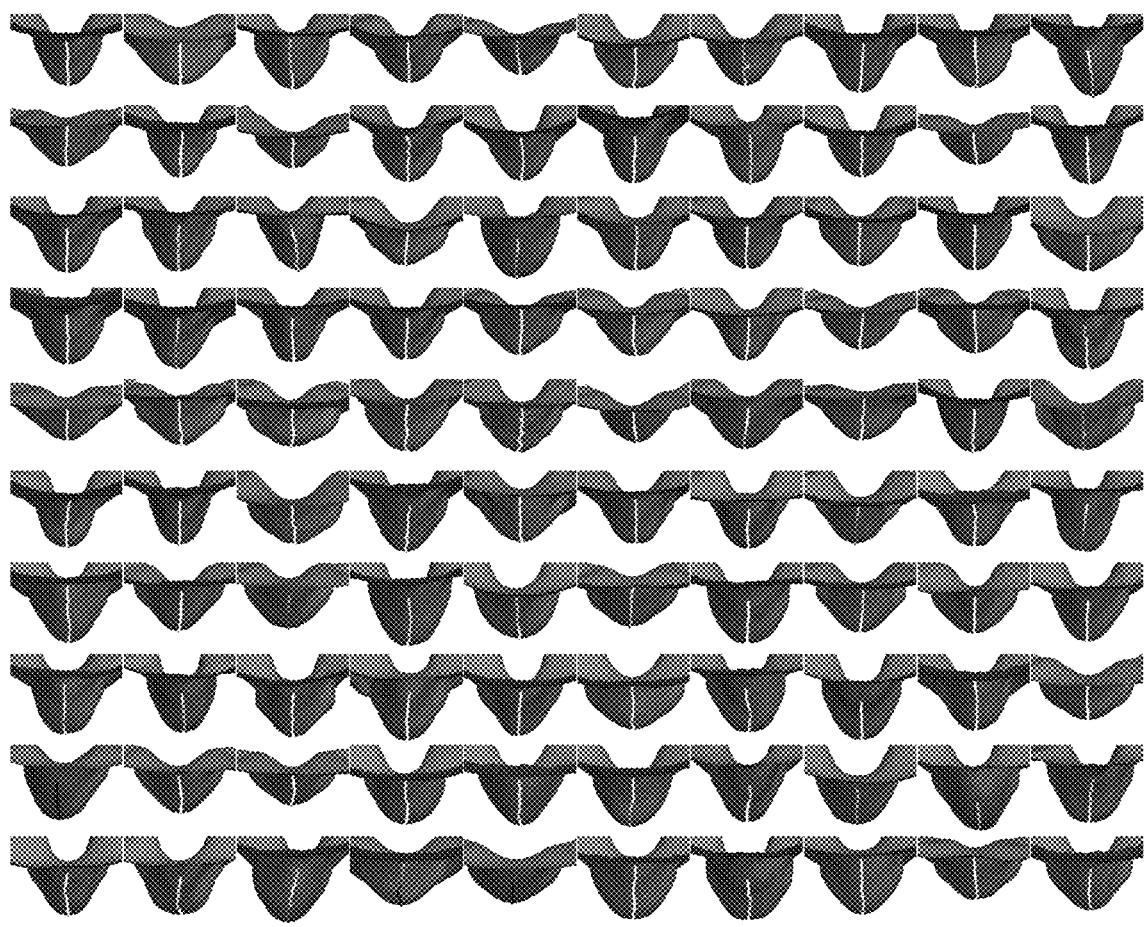
FIG. 15A shows nasal deviation measured for all subjects in the BU-3DFE database (top view) with the midline traced and the lateral distance from the median plane indicated on a magnitude colormap [−3.2 (blue) to 3.2 mm (red)].
Figure 15B:
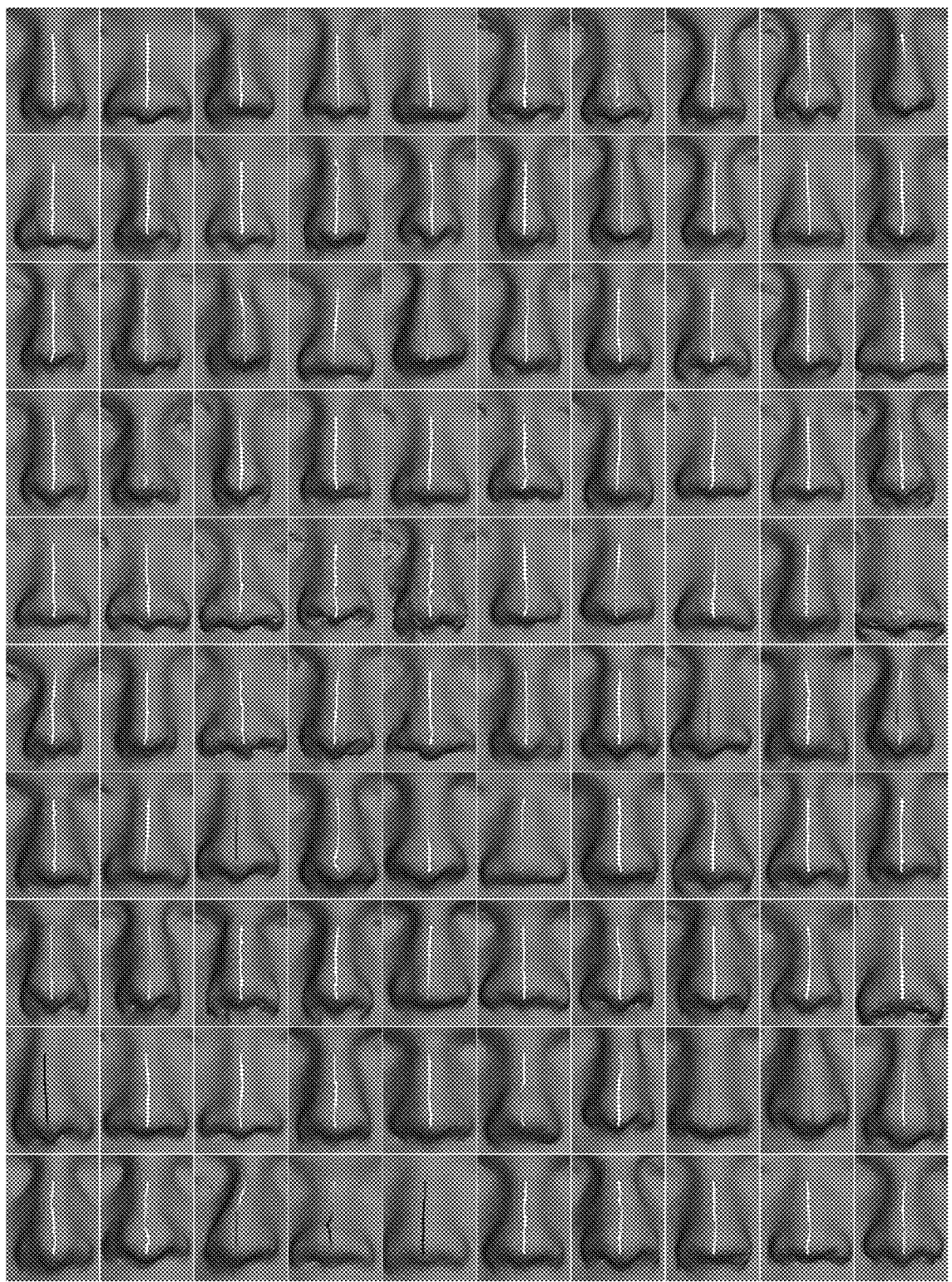
FIG. 15B shows nasal deviation measured for all subjects in the BU-3DFE database (front view) with the midline traced and the lateral distance from the median plane indicated on a magnitude colormap [−3.2 (blue) to 3.2 mm (red)].

Example 4: Nose Deviation Measurements of all 100 Subjects in the BU-3DFE Database FIGS. 15A and 15B shows montages illustrating the complete set of nasal deviation measurement results for all 100 subjects in the BU-3DFE database. In the 10×10 montages, subject #1 is located at the top-left corner and increase sequentially left to right and then top to bottom.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of assessing nasal symmetry, the method comprising:
    employing a surface scanning device to acquire facial surface data of a facial region of a subject, the facial region including a nose of the subject;
    processing the facial surface data to determine a nasal deviation measure indicative of a lateral deviation between a nasal midline of the subject and a facial midplane of the subject;
    processing the facial surface data to determine a nasal symmetry measure indicative of a degree of symmetry associated with a nasal surface region relative to the facial midplane; and
    generating a display comprising nasal deviation and symmetry information, the nasal deviation and symmetry information being generated based on both the nasal deviation measure and the nasal symmetry measure.

2. The method according to claim 1 further comprising, prior to determining the nasal deviation measure and the nasal symmetry measure, performing surface registration of the facial surface data with reference surface data, the reference surface data characterizing a reference symmetrical facial shape and having a facial direction, in a direction perpendicular to a coronal plane, aligned with a selected coordinate system, thereby generating transformed facial surface data aligned with the selected coordinate system, wherein the facial midplane is associated with the reference surface data.

3. The method according to claim 2 wherein the facial surface data further characterizes the maxilla-mandibular region.

4. The method according to claim 2 further comprising, prior to performing surface registration, removing nasal surface data from the facial surface data.

5. The method according to claim 2 wherein the nasal deviation measure is determined according to a lateral difference, within a transverse plane, perpendicular to the facial direction, between an estimated maximal dorsal projection of the transformed facial surface data within the transverse plane and the facial midplane.

6. The method according to claim 5 wherein the estimated maximal dorsal projection is determined by:
    generating a first segment extending laterally, within the transverse plane, perpendicular to the facial direction, and intersecting a nasal curve associated with the portion of the transformed facial surface data residing within the transverse plane at first intersection points, and obtaining a first midpoint location along the first segment between the first intersection points, the first segment being offset, in a posterior direction, by a first offset relative to a maximum anterior location of the nasal curve;
    generating a second segment extending laterally, within the transverse plane, perpendicular to the facial direction, and intersecting the nasal curve at second intersection points, and obtaining a second midpoint location along the second segment between the second intersection points, the second segment being offset, in the posterior direction, by a second offset relative to the maximum anterior location of the nasal curve; and
    determining the estimated maximal dorsal projection as the location of intersection between a third segment with the nasal curve, the first midpoint location and the second midpoint location residing on the third segment.

7. The method according to claim 5 wherein the nasal deviation measure comprises a plurality of lateral differences, each lateral difference being determined within a separate transverse plane.

8. The method according to claim 7 wherein the nasal deviation and symmetry information comprises a nasal midline curve generated based on the plurality of lateral differences.

9. The method according to claim 2 wherein the nasal symmetry measure is determined by:
    processing the nasal surface region to generate a mirrored nasal surface region, the mirrored nasal surface region residing on a contralateral side of the facial midplane; and
    processing the facial surface data and the mirrored nasal surface region to generate the nasal symmetry measure.

10. The method according to claim 9 wherein the nasal surface region is laterally shifted to compensate for nasal deviation prior to generating the mirrored nasal surface region.

11. The method according to claim 9 wherein the nasal surface region is user-defined.

12. The method according to claim 9 wherein the nasal surface region is an aesthetic subunit of the nose.

13. The method according to claim 12 wherein a surface region associated with the aesthetic subunit is automatically determined according to a pre-defined spatial region associated with the reference surface data.

14. The method according to claim 9 wherein the nasal symmetry measure is a single measure associated with the nasal surface region.

15. The method according to claim 14 wherein a plurality of nasal surface measures are generated for a respective plurality of nasal surface regions, each nasal surface region having a single associated nasal symmetry measure.

16. The method according to claim 2 further comprising:
employing a camera to obtain image data comprising the nose of the subject, the camera being rigidly mounted relative to the surface scanning device;
processing the image data such that the image data is represented in a common coordinate system with the transformed facial surface data; and
generating, within the common coordinate system, augmented reality annotation data associated with one or both of the nasal deviation measure and the nasal symmetry measure; and
generating and displaying an image comprising the image data and the augmented reality annotation data.

17. The method according to claim 16 wherein the augmented reality annotation data comprises directional information indicating a direction suitable for correcting a local nasal deviation or local nasal asymmetry.

18. The method according to claim 1 wherein the surface scanning device is a handheld surface scanning device.

19. The method according to claim 1 wherein the facial surface data is acquired intraoperatively during a medical procedure, and wherein the nasal deviation and symmetry information is displayed intraoperatively during the medical procedure.

20. A system for assessing nasal deviation and symmetry, the system comprising:
a surface scanning device; and
control and processing circuitry operatively coupled to said surface scanning device, said control and processing circuitry comprising at least one processor and associated memory, said memory comprising instructions executable by said at least one processor for performing operations comprising:
controlling said surface scanning device to acquire facial surface data of a facial region of a subject, the facial region including a nose of the subject;
processing the facial surface data to determine a nasal deviation measure indicative of a lateral deviation between a nasal midline of the subject and a facial midplane of the subject;
processing the facial surface data to determine a nasal symmetry measure indicative of a degree of symmetry associated with a nasal surface region relative to the facial midplane; and
generating a display comprising nasal deviation and symmetry information, the nasal deviation and symmetry information being generated based on both the nasal deviation measure and the nasal symmetry measure.

* * * * *